(12) United States Patent
West et al.

(10) Patent No.: US 7,635,592 B2
(45) Date of Patent: Dec. 22, 2009

(54) TISSUE ENGINEERING SCAFFOLDS PROMOTING MATRIX PROTEIN PRODUCTION

(75) Inventors: Jennifer L. West, Pearland, TX (US); Brenda K. Mann, Upland, CA (US)

(73) Assignee: Rice University, Houston, TX (US)

( * ) Notice: Subject to any disclaimer, the term of this patent is extended or adjusted under 35 U.S.C. 154(b) by 943 days.

(21) Appl. No.: 09/935,168

(22) Filed: Aug. 21, 2001

(65) Prior Publication Data

US 2002/0106793 A1 Aug. 8, 2002

Related U.S. Application Data

(60) Provisional application No. 60/226,771, filed on Aug. 21, 2000.

(51) Int. Cl.
- *C12N 5/06* (2006.01)
- *C12N 5/08* (2006.01)
- *G01N 33/567* (2006.01)
- *A61K 39/385* (2006.01)

(52) U.S. Cl. ............... 435/395; 435/366; 435/7.21; 530/816; 424/9.322; 424/193.1; 424/195.11

(58) Field of Classification Search ............ 435/382; 424/422, 428, 486, 490
See application file for complete search history.

(56) References Cited

U.S. PATENT DOCUMENTS

| | | | |
|---|---|---|---|
| 5,162,430 A * | 11/1992 | Rhee et al. ............. | 525/54.1 |
| 5,686,091 A | 11/1997 | Leong et al. | |
| 5,916,585 A | 6/1999 | Cook et al. | |
| 5,935,849 A * | 8/1999 | Schinstine et al. ....... | 435/325 |
| 6,013,853 A | 1/2000 | Athanasiou et al. | |
| 6,017,301 A | 1/2000 | Schwartz et al. | |
| 6,022,743 A | 2/2000 | Naughton et al. | |
| 6,077,523 A | 6/2000 | Deghenghi | |

FOREIGN PATENT DOCUMENTS

| | | |
|---|---|---|
| EP | 00428541 B1 | 5/1991 |
| EP | 0616814 A1 | 9/1994 |
| WO | WO 92/20371 | 11/1992 |
| WO | WO 94/01483 | 1/1994 |
| WO | WO 94/23740 | 10/1994 |
| WO | WO 96/27657 | 9/1996 |

OTHER PUBLICATIONS

Dinbergs et al, J Biol Chem 271(47): 29822-29, 1996.*
Scott-Burden et al, J Cardiovasc Pharmacol 16 Suppl 4: S36-41, 1990, Abstract only.*
Stryer et al, in Biochemistry, Third edition, W H Freeman Company, New York, pp. 31-33, 1998.*
Scott-Burden et al, J Cardiovasc Pharmacol 17(7): S96-100, 1991.*
Nabel, et al., "Direct transfer of transforming growth factor beta 1 gene into arteries stimulates fibrocellular hyperplasia" *Proc. Natl. Acad. Sci. USA* 90(22):10759-10763 (1993).
Nicoll, et al., "In vitro characterization of transforming growth factor-beta-1-loaded composites of biodegradable polymer and mesenchymal cells" *Cells and Materials* 5(3): 231-244 (1995).
Pandit, et al., "The effect of TGF-beta delivered through a collagen scaffold on wound healing" *J. Invest. Surg.* 12(2):89-100 (1999).
Plenz, et al., "Colony stimulating factors modulate the transcription of type VIII collagen in vascular smooth muscle cells" *Atherosclerosis* 144(1):25-32 (1999).
Puolakkainen, et al., "The enhancement in wound healing by transforming growth factor-beta 1 (TGF-beta 1) depends on the topical delivery system" *J. Surg. Res.* 58(3):321-329 (1995).
Schroeder-Tefft, et al., "Collagen and heparin matrices for growth factor delivery" *Journal of Controlled Release* 49(2-3): 291-298 (1997).
Scott-Burden, et al., "Epidermal growth factor responsiveness in smooth muscle cells from hypertensive and normotensive rats" *Hypertension* 13(4):295-305 (1989).
Tong et al.,"Peptide surface modification of poly(tetrafluoroethylene-co-hexafluoropropylene) enhances its interaction with central nervous system neurons" *J. Biomed. Mater. Res.* 42(1):85-95 (1998).
Woessner, et al., "The determination of hydroxyproline in tissue and protein samples containing small proportions of this imino acid" *Arch. Biochem. Biophys.* 93:440-447 (1961).
Zhang, et al., "Biological surface engineering: a simple system for cell pattern formation" *Biomaterials* 20(13):1213-1220 (1999).
Amento, et al., "Cytokines and growth factors positively and negatively regulate interstitial collagen gene expression in human vascular smooth muscle cells" *Arterioscler. Thromb.* 11(5):1223-1230 (1991).
Clark, et al., "Collagen matrices attenuate the collagen-synthetic response of cultured fibroblasts to TGF-beta" *J. Cell Sci.* 108(PT3):1251-1261 (1995).
Dee, et al., "Design and function of novel osteoblast-adhesive peptides for chemical modification of biomaterials" *J. Biomed. Mater. Res.* 40(3):371-377 (1998).
Eickelberg, et al., "Extracellular matrix deposition by primary human lung fibroblasts in response to TGF-beta1 and TGF-beta3" *Am. J. Physiol.* 276(5 Pt 1):L814-L824 (1999).
Heimer, et al., "TGF-beta modulates the synthesis of proteoglycans by myocardial fibroblasts in culture" *J. Mol. Cell Cardiol.* 27(10):2191-2198 (1995).

(Continued)

*Primary Examiner*—Phuong Huynh
(74) *Attorney, Agent, or Firm*—Baker Botts L.L.P.

(57) ABSTRACT

Matrix-enhancing molecules, such as TGF-β, are conjugated to or immobilized on scaffolds to increase ECM production by cells for tissue engineering, tissue regeneration and wound healing applications. The matrix-enhancing molecule is conjugated to a tether, such as polyethylene glycol (PEG) monoacrylate, for attachment to a tissue engineering or cell growth scaffold. The matrix-enhancing molecule retains activity after attachment to the scaffold, and causes cells growing in or on the scaffold to increase extracellular matrix (ECM) production, without substantially increasing proliferation of the cells, even when the scaffold additionally contains cell adhesion ligands. The increased ECM produced by the cells aids in maintaining the integrity of the scaffold, particularly when the scaffold is degradable, either by hydrolysis or by enzymatic degradation.

20 Claims, 4 Drawing Sheets

OTHER PUBLICATIONS

Hern et al., "Incorporation of adhesion peptides into nonadhesive hydrogels useful for tissue resurfacing" *J. Biomed. Mater. Res.* 39(2):266-276 (1998).

Jones, et al., "Glycoprotein, elastin, and collagen secretion by rat smooth muscle cells" *Proc. natl. Acad. Sci. USA* 76(1):353-357 (1979).

Lawrence, et al., "Transforming growth factor beta 1 stimulates type V collagen expression in bovine vascular smooth muscle cells" *J. Biol. Chem.* 269:9603-9609 (1994).

Majesky, et al., "Production of transforming growth factor beta 1 during repair of arterial injury" *J. Clin. Invest.* 88(3):904-910 (1991).

Mann, et al., "Modification of surfaces with cell adhesion peptides alters extracellular matrix deposition" *Biomaterials* 20(23-24):2281-2286 (1999).

Massia et al., "Covalent surface immobilization of Arg-Gly-Asp- and Tyr-Ile-Gly-Ser-Arg-containing peptides to obtain well-defined cell-adhesive substrates" *Anal. Biochem.* 187(2):292-301 (1990).

Hoerstrup, et al., "Tissue Engineering of a Bioprosthetic Heart Valve: Stimulation of Extracellular Matrix Assessed by Hydroxyproline Assay," *ASAIO Journal* 45(5): 397-402 (1999).

Mann, et al., "Tethered-TGF—Beta increases extracellular matrix production of vascular smooth muscle cells," *Biomaterials* 22(5): 439-444 (2001).

PCT International Preliminary Examination Report mailed Mar. 4, 2003.

EPO Communication pursuant to Article 96(2) EPC, dated May 24, 2004.

EPO Communication pursuant to Article 96(3) EPC, Mar. 6, 2006.

* cited by examiner

SEQUENCE LISTING

```
<160> NUMBER OF SEQ ID NOS: 4

<210> SEQ ID NO 1
<211> LENGTH: 4
<212> TYPE: PRT
<213> ORGANISM: artificial sequence
<220> FEATURE:
<223> OTHER INFORMATION: cell adhesion ligand

<400> SEQUENCE: 1

Arg Gly Asp Ser
1

<210> SEQ ID NO 2
<211> LENGTH: 4
<212> TYPE: PRT
<213> ORGANISM: artificial sequence
<220> FEATURE:
<223> OTHER INFORMATION: cell adhesion ligand

<400> SEQUENCE: 2

Val Ala Pro Gly
1

<210> SEQ ID NO 3
<211> LENGTH: 6
<212> TYPE: PRT
<213> ORGANISM: artificial sequence
<220> FEATURE:
<223> OTHER INFORMATION: cell adhesion ligand

<400> SEQUENCE: 3

Lys Gln Ala Gly Asp Val
1               5

<210> SEQ ID NO 4
<211> LENGTH: 4
<212> TYPE: PRT
<213> ORGANISM: artificial sequence
<220> FEATURE:
<223> OTHER INFORMATION: cell adhesion ligand

<400> SEQUENCE: 4

Arg Gly Glu Ser
1
```

TISSUE ENGINEERING SCAFFOLDS PROMOTING MATRIX PROTEIN PRODUCTION

This application claims priority to U.S. Ser. No. 60/226,771 filed Aug. 21, 2000.

BACKGROUND OF THE INVENTION

This is generally in the field of improved compositions for tissue engineering, specifically scaffolds incorporating defined densities of matrix-enhancing molecules for improving matrix protein production of cells, without inducing excessive proliferation of the cells.

In fields where cell growth, maintenance, or production of exogenous factors are important, such as in the field of tissue engineering, cells are often grown on solid substrates or scaffolds which provide a suitable substrate for cell adhesion and growth. These scaffolds may be made of natural or synthetic materials.

Biomaterials developed for tissue engineering and wound healing applications need to support adequate cell adhesion while being replaced by new tissue synthesized by those cells. In order to maintain proper mechanical integrity of the tissue, the cells must generate sufficient extracellular matrix (ECM). Decreased ECM production by cells in tissue engineering scaffolds may lead to reduced structural integrity of the developing tissue.

In order to optimally promote adhesion to such materials, researchers have investigated attachment of cell adhesion ligands, such as the RGD peptide, to surfaces of biomaterials (Massia & Hubbell, Anal. Biochem. 187:292-301 (1990); Hem & Hubbell, J. Biomed. Mater. Res. 39:266-276 (1998); Dee, et al. J. Biomed. Mater. Res. 40:371-377 (1998); Tong & Shoichet, J. Biomed. Mater. Res. 42:85-95 (1998); Zhang, et al., Biomaterials 20:1213-1220 (1999)). However, an increase in cell adhesion can adversely affect ECM production (Mann, et al., Biomaterials 1999). In addition, there exists a substantial need to increase ECM production, even in unmodified scaffolds, as the proteins in the ECM largely determine the mechanical properties of the resultant tissue and are often needed to replace the functions of a biodegradable scaffold material. The mechanical properties of the resultant tissue are particularly important in applications such as tissue engineered vascular grafts and orthopedic tissue engineering wherein failure can occur due to poor mechanical integrity.

Researchers have also attached growth factors such as TGF to a tissue engineering matrix via a polymeric tether such as a polyethylene glycol. See PCT/US96/02851 "Cell Growth Substrates with Tethered Cell Growth Effector Molecules" Massachusetts Institute of Technology. There are a number of references that TGF-beta can be bound to or dispersed within a synthetic or natural polymeric carrier for controlled release of active growth factor. See, for example, "Collagen and heparin matrices for growth factor delivery", Schroeder-Tefft, et al. Journal of Controlled Release 49(2-3), 291-298 (1997); "In vitro characterization of transforming growth factor-beta-1-loaded composites of biodegradable polymer and mesenchymal cells. Nicoll, et al. *Cells and Materials* 5(3), 231-244 (1995). EP 00428541"Collagen Wound healing Matrices and Process for their Production" to Collagen Corporation; U.S. Pat. No. 6,013,853 "Continuous release polymeric implant carrier" to Athanasiou, et al. Additional reference relate to the use of TGF-beta in tissue engineering scaffolds to enhance cell or tissue growth or proliferation, particularly of bone. See EP 616814 "Ceramic and Polymer-Based Compositions for Controlled Release of Biologically Active TGF-Beta to Bone Tissue, and Implants Using The Compositions" by Bristol-Myers Squibb Company.

However, none of these disclosures disclose how one can achieve enhanced production of extracellular matrix, while not increasing cellular proliferation.

It is therefore an object of the present invention to provide tissue engineering scaffolds which promote formation of ECM, to enhance the formation of tissue with good mechanical properties, on and within the tissue engineering scaffold, i.e., with little or no increase in cellular proliferation.

SUMMARY OF THE INVENTION

It has been found that matrix-enhancing molecules, such as transforming growth factor-beta (TGF-$\beta$), can be conjugated to or immobilized on scaffolds to increase ECM production by cells. The matrix-enhancing molecule is conjugated to a polymer, such as polyethylene glycol (PEG) monoacrylate, for attachment to a tissue engineering or cell growth scaffold, useful in not only tissue engineering but also for tissue regeneration and wound healing applications. The matrix-enhancing molecule retains activity after attachment to the scaffold, and causes cells growing in or on the scaffold to increase ECM production, even when the scaffold additionally contains cell adhesion ligands. This increase in ECM production is believed to be due to an increase in gene expression, not cell proliferation. The increased ECM produced by the cells aids in maintaining the integrity of the scaffold, particularly when the scaffold is degradable, either by hydrolysis or by enzymatic degradation.

The examples demonstrate that matrix production by vascular smooth muscle cells (SMCs) grown in a polymer scaffold, which was formed from PEG hydrogels, containing covalently bound adhesive ligands was increased in the presence of $4 \times 10^{-5}$ nmol TGF-$\beta$/ml tethered to the scaffold over when no TGF-$\beta$ was present. At the same time cell proliferation was not increased, which is advantageous since increased proliferation of SMCs could lead to narrowing of a vessel lumen. Tethering TGF-$\beta$ to the polymer scaffold resulted in a significant increase in extracellular matrix production over the same amount of soluble TGF-$\beta$ (see Example 1, FIG. 3). This is most likely due to internalization of the soluble TGF-$\beta$ by the cells or diffusion of the soluble TGF-$\beta$ from the hydrogels, making the TGF-$\beta$ unavailable to the cells.

DETAILED DESCRIPTION OF THE INVENTION

Tissue engineering is performed using a scaffold material that allows for attachment of cells. The scaffold material contains a matrix enhancing molecule. As described herein, the matrix-enhancing molecule should promote the production of extracellular matrix proteins, but should not promote cell proliferation.

Scaffold Materials

In the preferred embodiment, the scaffold is formed of synthetic or natural polymers, although other materials such as hydroxyapatite, silicone, and other inorganic materials can be used. The scaffold may be biodegradable or non-degradable.

There are a number of biocompatible polymers, both degradable and non-degradable. Representative synthetic non-biodegradable polymers include ethylene vinyl acetate and poly(meth)acrylate. Representative biodegradable polymers include polyhydroxyacids such as polylactic acid and polyglycolic acid, polyanhydrides, polyorthoesters, and copolymers thereof. Natural polymers include collagen, hyaluronic acid, and albumin.

A preferred material is a hydrogel. A particularly preferred hydrogel forming material is a polyethylene glycol-diacrylate polymer, which is photopolymerized. Other hydrogel materials include calcium alginate and certain other polymers that can form ionic hydrogels that are malleable and can be used to encapsulate cells.

Formation of Scaffolds

Scaffolds can be formed in situ or in vitro. In a preferred embodiment for formation of joint linings, the scaffold material is sprayed in a dilute solution onto the joint, then polymerized, so that the polymer forms a hydrogel coating bonded onto the surface of the joint tissues. Cells can be dispersed within the polymer, or seeded onto the polymeric matrix. Scaffolds may also be formed of fibers of polymer, woven or non-woven into meshes that can be used to support cell attachment and growth. These scaffolds can be formed by casting, weaving, salt leaching, spinning, or molding. In still another embodiment, scaffolds can be formed using molds formed by micromachining and photolithographic techniques, where the cells can be seeded into the scaffold while in the molds or after removal of the scaffold. In a preferred embodiment, a liquid cell-polymer solution is placed in a mold and photopolymerized, converting the liquid to a hydrogel with the cells seeded within the hydrogel.

The scaffolds can be seeded at the time of or before implantation at a site where tissue is desired. Meshes should preferably be sufficiently open to allow free diffusion of nutrients and gases throughout the scaffold.

Matrix-Enhancing Molecules

Matrix-enhancing molecules which promote increased production of ECM can be attached to the scaffold material to induce production of matrix proteins, such as glycoproteins, elastin, and collagen, without substantially increasing cell proliferation. These matrix-enhancing molecules include TGF-β, angiotensin II, insulin-like growth factors and ascorbic acid.

TGF-β is known to increase production of extracellular matrix proteins by vascular SMCs growing in culture (Amento, et al. Arterioscler. Thromb. 11:1223-1230 (1991); Lawrence, et al., J. Biol. Chem. 269:9603-9609 (1994); Plenz, et al., Atherosclerosis 144:25-32 (1999)). TGF-β, through production by SMCs naturally during vessel injury or by gene transfer, can also increase ECM production by SMCs in vivo (Majesky, et al., J. Clin. Invest. 88:904-910 (1991); Nabel, et al., Proc. Natl. Acad. Sci. USA 90:10759-10763 (1993)). Cultured fibroblasts have also been shown to increase collagen synthesis (Clark, et al., J. Cell Sci. 108: 1251-1261 (1995); Eickelberg, et al., Am. J. Physiol. 276: L814-L824 (1999)) and proteoglycan synthesis (Heimer, et al., J. Mol. Cell Cardiol. 27:2191-2198 (1995)) in the presence of TGF-β. Further, topical delivery of TGF-β (Puolakkainen, et al., J. Surg. Res. 58:321-329 (1995)) and delivery to TGF-β through a collagen scaffold (Pandit, et al., J. Invest. Surg. 12:89-100 (1999)) have been shown to enhance wound healing.

All of the above-referenced studies have examined effects in the presence of soluble TGF-β. As demonstrated by the following examples, it has now been shown that tethered TGF-β can also be used to induce formation of ECM by cells, including cells such as smooth muscle cells and chondrocytes.

Tethers

For the matrix-enhancing molecules to induce formation of ECM, it is necessary for the molecule to be tethered to the scaffold by a tether. These tethers have a molecular weight of preferably between about 200 and 10,000, most preferably between about 2000 and 6,000. The tether is preferably a linear polymer, such as polyethylene glycol. The matrix-enhancing molecule may be coupled to the tether, or for that matter, to the scaffold material, by any method known to those of skill in the art, preferably covalently coupled using a reagent such as n-hydroxysuccinimide, carbodiimide, diisocyanate, carbonyldiamidazole, or tosyl chloride.

Density of Matrix-Enhancing Materials

The density of the matrix-enhancing materials is important in eliciting ECM production with little or no cellular proliferation. The amount of ECM production that is most desirable is that which results in formation of tissue with good mechanical properties, on and within the tissue engineering scaffold. The optimal density will depend on the type of cells to be attached to the scaffold. In the case of TGF-β, optimal concentrations to induce ECM production is in the range of between one and five ng TGF-β/ml for aortic smooth muscle cells and between 5 and 100 ng TGF-β/ml for auricular chondrocytes, which is equivalent to between $4 \times 10^{-6}$ and $4 \times 10^{-3}$ nmol/ml.

Source of Cells

Cells can be obtained directly from a donor, from a culture of cells from a donor, or from established cell culture lines. In the preferred embodiment, cells of the same species and, preferably having the same or a similar immunological profile, are obtained by biopsy, either from the patient or a close relative, which can then be grown in culture using standard conditions. If cells that are likely to elicit an immune reaction are used, such as human muscle cells from an immunologically distinct individual, then the recipient can be immunosuppressed as needed, for example, using a schedule of steroids and other immunosuppressant drugs, such as cyclosporine.

In the preferred embodiments, cells are obtained directly from a donor, washed and implanted directly in combination with the polymeric material. The cells are cultured using techniques known to those skilled in the art of tissue culture. Cells obtained by biopsy are harvested and cultured, passaging as necessary to remove contaminating cells.

Preferred cells for formation of vascular tissue include smooth muscle cells, endothelial cells, and fibroblasts. Preferred cells for formation of connective tissue include chondrocytes, fibroblasts, and other types of cells that differentiate into bone or cartilage.

Methods of Using the Scaffolds

The scaffolds are used to produce new tissue, such as vascular tissue, cartilage, tendons, and ligaments. The scaffold is typically seeded with the cells; the cells are cultured; and then the scaffold implanted. Alternatively, as noted above, the scaffold is sprayed into or onto a site such as a joint lining, seeded with cells, and then the site is closed surgically. Liquid polymer-cell suspensions can also be injected into a site, such as within a joint, where the material may be polymerized.

Applications include the repair and/or replacement of organs or tissues, such as blood vessels, cartilage, joint linings, tendons, or ligaments, or the creation of tissue for use as "bulking agents", which are typically used to block openings or lumens, or to shift adjacent tissue, as in treatment of reflux.

The present invention will be further understood by reference to the following non-limiting examples.

EXAMPLE 1

Comparison of Effect of Soluble and Bound TGF-β in Combination with PEG-Diacrylate Hydrogel It was determined whether TGF-β can counteract the decrease in ECM synthesis caused by immobilized cell adhesion ligands. SMCs were grown on both peptide-modified glass substrates and in hydrogels containing tethered cell adhesion ligands. Further, TGF-β was covalently tethered to a polymer scaffold and shown that it retains its ability to increase ECM production.

Materials & Methods

Cell Maintenance

Chemicals were obtained from Sigma Chemical Co. (St. Louis, Mo.) unless otherwise stated. SMCs from the thoracic aorta of Wistar-Kyoto rats were isolated and characterized as previously described by Scott-Burden, et al., Hypertension 13:295-305 (1989). Human aortic smooth muscle cells (HASMCs) were obtained from Clonetics (San Diego, Calif.). Both SMCs and HASMCs were maintained on Minimal Essential Medium Eagle supplemented with 10% fetal bovine serum (FBS; BioWhittaker, Walkersville, Md.), 2 mM L-glutamine, 500 units penicillin and 100 mg/l streptomycin (MEM). Cells were incubated at 37° C. in a 5% $CO_2$ environment.

Surface Modification

Peptides used in this study were RGDS (SEQ ID NO:1), VAPG (SEQ ID NO:2), and KQAGDV (SEQ ID NO:3) (Research Genetics, Huntsville, Ala.). RGES (SEQ ID NO:4) was used as a non-adhesive control peptide. The peptides were acetylated and coupled to aminophase glass slides as previously described by Mann, et al., Biomaterials 20:2281-2286 (1999). Briefly, aminophase slides were prepared by incubating glass slides with 3-aminopropyltriethoxysilane in dry acetone at 37° C. overnight. Acetylated peptides were then coupled to the slides using 1-ethyl-3-(3-dimethylaminopropyl) carbodiimide (EDAC) chemistry. Slides were sterilized under UV light overnight prior to use.

Preparation of Acryloyl-PEG-TGF-β

TGF-β was conjugated to polyethylene glycol (PEG) by reacting TGF-β with acryloyl-PEG-N-hydroxysuccinimide (acryloyl-PEG-NHS, 3400 Da; Shearwater Polymers, Huntsville, Ala.) in 50 mM TRIS buffer (pH 8.5) for 2 hr. The mixture was then lyophilized and stored frozen. Gel permeation chromatography equipped with UV/Vis (260 nm) and evaporative light scattering detectors was used to analyze the resulting acryloyl-PEG-TGF-β and PEG standards (Polymer Laboratories, Amherst, Me.).

Evaluation of Matrix Protein Production on Surfaces.

Matrix protein production was evaluated as previously described by Mann (1999). Suspensions of SMCs were prepared in MEM supplemented with 5 μg/ml ascorbic acid at a concentration of 40,000 cells/ml. For samples receiving TGF-β, 0.04 pmol/ml (1 ng/ml) unmodified TGF-β or 0.04 pmol/ml acryloyl-PEG-TGF-β was added to the media. Cell suspensions to be used for measurement of ECM protein production were also supplemented with 1 μCi/ml $^3$H-glycine (40 Ci/mmol). The glass slides were attached to FlexiPerm strips in QuadriPerm Cell Culture Vessels (Heraeus, Osterode am Harz, Germany) to create eight wells (1.11×0.79×0.79 cm) on each slide. Four of the wells on each slide were utilized to measure ECM production, while the remaining four wells were utilized for cell number determination and were cultured in the absence of $^3$H-glycine. Cell number was determined after 2 days of culture by preparing single cell suspensions using trypsin and counting cells using a Coulter counter (Multisizer #0646, Coulter Electronics, Hialeah, Fla.).

To evaluate synthesis of ECM proteins, the cell growth media was supplemented with $^3$H-glycine, as described above. Two days following $^3$H-glycine addition, cells were removed non-enzymatically with 25 mM ammonium hydroxide, then rinsed with 70% ethanol and dried. This process leaves intact the ECM elaborated by cells during culture (Jones, et al., Proc. natl. Acad. Sci. USA 76:353-357 (1979)). Sequential enzyme digestion was used as previously described by Mann (1999) to determine the gross composition of the ECM proteins. Briefly, the ECM was digested first with trypsin, followed by elastase, and then collagenase. After the final enzymatic digestion, any material remaining on the substrate was dissolved by incubation with 1 N NaOH. Aliquots were taken from each step of the digest for scintillation counting.

Preparation of Acryloyl-PEG-RGDS (SEQ ID NO:1)

RGDS (SEQ ID NO:1) was conjugated to acryloyl-PEG-NHS in the same manner as TGF-β.

Preparation of PEG-Diacrylate

PEG-diacrylate was prepared by combining 0.1 mmol/ml dry PEG (6,000 Da; Fluka, Milwaukee, Wis.), 0.4 mmol/ml acryloyl chloride, and 0.2 mmol/ml triethylamine in anhydrous dichloromethane and stirring under argon overnight. The resulting PEG-diacrylate was then precipitated with ether, filtered, and dried in a vacuum oven.

Preparation of Hydrogels

Hydrogels were prepared by combining 0.4 g/ml PEG-diacrylate, 1.4 µmol/ml acryloyl-PEG-RGDS (SEQ ID NO:1), and 0.3 mmol/ml triethanolamine in 10 mM HEPES-buffered saline (pH 7.4, HBS). This aqueous polymer solution was sterilized by filtration (0.8 µm prefilter and 0.2 µm filter) and added to an equal volume of a suspension of SMCs at $2\times10^6$ cells/ml, such that the resulting polymer-cell solution contained $1\times10^6$ cells/ml. For hydrogels containing TGF-β, 0.04 pmol/ml (1 ng/ml) unmodified TGF-β or 0.04 pmol/ml acryloyl-PEG-TGF-β was added to the polymer-cell solution. Then, 40 µl of 2,2-dimethyl-2-phenyl-acetophenone in n-vinylpyrrolidone (600 mg/ml) was added, and 0.25 ml of the solution was placed in a disk-shaped mold (20 mm diameter, 2 mm thickness). This liquid polymer-cell solution was then exposed to UV light (365 nm, 10 mW/cm$^2$) for 20 sec to convert the liquid polymer-cell solution to a hydrogel with homogeneously seeded cells. Hydrogels were incubated in MEM containing 10% FBS for 7 days at 37° C. with 5% $CO_2$. Media was changed every 3 days.

DNA and Hydroxyproline Determination in Hydrogels

After 7 days of culture, hydrogels were removed from the culture media, weighed, and digested with 1 ml 0.1 N NaOH overnight at 37° C. Digested hydrogels were then neutralized with 1 ml 0.1 N HCl. DNA content of the digested, neutralized hydrogels was determined using a fluorescent DNA binding dye, Hoechst 33258 (Molecular Probes, Eugene, Oreg.). Fluorescence of the samples was determined using a fluorometer (VersaFluor, Bio-Rad Laboratories, Hercules, Calif.) with excitation filter at 360 nm and emission filter at 460 nm, and compared to fluorescence of calf thymus DNA standards.

Hydroxyproline concentration was determined by oxidation with chloramine T (ICN Biomedicals, Aurora, Ohio) and development with p-dimethylaminobenzaldehyde (ICN Biomedicals) (Woessner, et al. Arch. Biochem. Biophys. 93:440-447 (1961)). Hydroxyproline is a marker for collagen production, and thus was used as an indication of matrix synthesis.

Mechanical Testing of Hydrogels

Hydrogels were prepared as described above, except that 2 ml of the liquid polymer-cell solution was placed in a 3 mm thick rectangular mold (42 mm×14 mm). For this experiment, HASMCs were used at a final cell density of $3.5\times10^5$ cells/ml. Hydrogels contained either no TGF-β or 0.04 pmol/ml acryloyl-PEG-TGF-β.

Following photopolymerization, the hydrogels were placed in QuadriPerm Cell Culture Vessels with 10 ml media containing 10% FBS and incubated at 37° C. with 5% $CO_2$. Media was changed every 3 days. After 7 days of culture, the hydrogels were cut into 3 sections (14 mm×14 mm), and mechanical testing was performed using a Vitrodyne V-1000 Universal Tester (Chatillon, Greensboro, N.C.) at a strain rate of 100 µm/s using a 150 g loading cell.

Statistical Analysis

Data sets were compared using two-tailed, unpaired t-tests. P-Values less than 0.05 were considered to be significant.

Results

Figure 1:
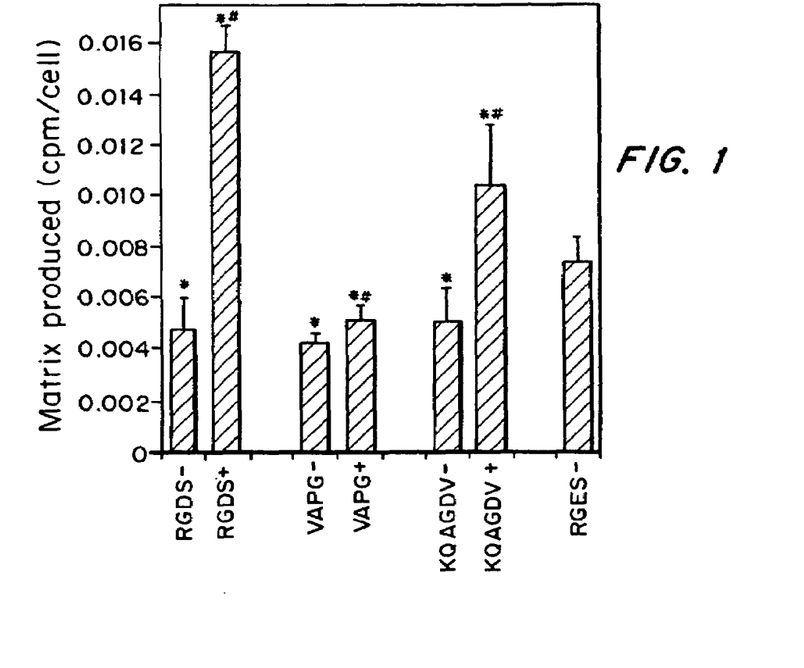
FIG. 1 is a graph of matrix production per cell by SMCs growing on glass surfaces covalently coupled with RGDS (SEQ ID NO:1), VAPG (SEQ ID NO:2), KQAGDV (SEQ ID NO:3), or RGES (SEQ ID NO:4) with and without TGF-$\beta$ in the media. The "+" indicates that TGF-$\beta$ was added to the media, while the "−" indicates that TGF-$\beta$ was absent from the media.

The goal of the current study was to determine whether TGF-β can enhance the rate of ECM synthesis by cells grown on or in biomaterials, particularly materials that have been modified with cell adhesion ligands. FIG. 1 shows the matrix protein production on a per cell basis for cells grown with either no TGF-β or 0.04 pmol/ml (1 ng/ml) soluble TGF-β in the media. With no TGF-β in the media, more matrix was produced by cells growing on the non-adhesive control, RGES (SEQ ID NO:4), than on the adhesive peptides. When TGF-β was added to the media, matrix production increased on the adhesive surfaces over that produced when no TGF-β was added (224% increase on RGDS (SEQ ID NO:1) surfaces, 20% increase on VAPG (SEQ ID NO: 2) surfaces, 104% increase on KQAGDV (SEQ ID NO:3) surfaces). Matrix production on the RGDS (SEQ ID NO:1) and KQAGDV (SEQ ID NO:3) modified surfaces in the presence of TGF-β increased over that seen with the non-adhesive control.

Figure 2:
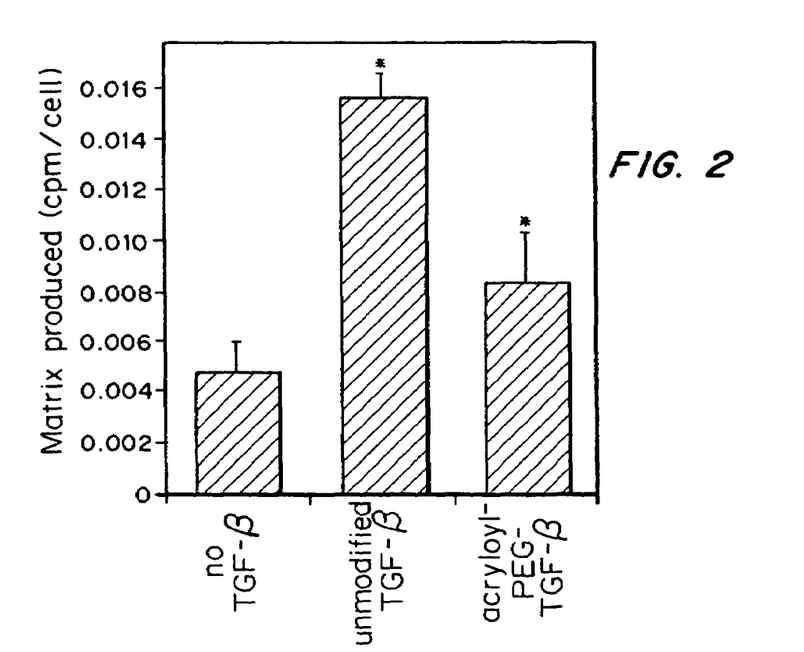
FIG. 2 is a graph of matrix production per cell by SMCs growing on RGDS (SEQ ID NO:1)-modified glass surfaces with no TGF-$\beta$, soluble TGF-$\beta$ or acryloyl-PEG-TGF-$\beta$ at $4 \times 10^{-5}$ nmol/ml in the hydrogel. The control is with no TGF-$\beta$ in the hydrogel.

Cells seeded onto RGDS (SEQ ID NO:1)-modified glass surfaces were also grown in the presence of 0.04 pmol/ml acryloyl-PEG-TGF-β to determine if TGF-β could be covalently bound to a polymer (covalently attached to a soluble polymer chain but not tethered to a three dimensional structure) and retain its ability to increase ECM production. FIG. 2 shows the matrix production by cells grown with no TGF-β, soluble TGF-β, or acryloyl-PEG-TGF-β in the media. SMCs produced greater amounts of matrix in the presence of either soluble or polymer-conjugated TGF-β over that produced in the absence of TGF-β. However, less matrix was produced when polymer-conjugated TGF-β was used than when unmodified TGF-β was used.

SMCs were then homogeneously seeded into polyethylene glycol (PEG) hydrogels containing covalently tethered RGDS (SEQ ID NO:1). The hydrogels contained either no TGF-β, unmodified (soluble) TGF-β, or PEG-tethered TGF-β. In these photopolymerized hydrogels, the tethered peptides of TGF-β are covalently bound to the hydrogel structure via a highly flexible PEG chain. This gives the tethered moieties conformational freedom to interact with their receptors while causing them to be retained in the hydrogel material. After 7 days of culture, the hydrogels were digested and assayed for DNA and hydroxyproline. Since hydroxyproline is a marker for collagen, it is an indication of how much extracellular matrix has been produced.

Figure 3:
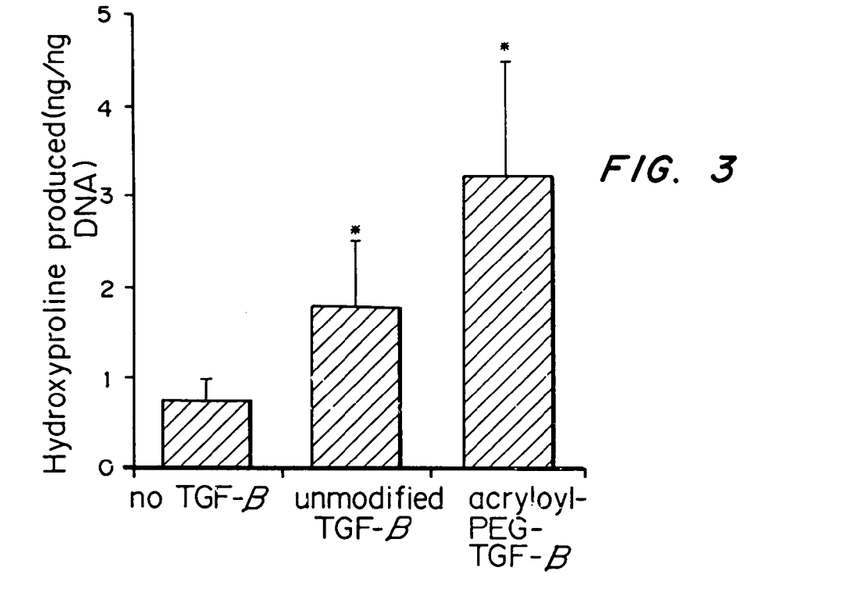
FIG. 3 is a graph of hydroxyproline production per ng of DNA by SMCs growing in RGDS (SEQ ID NO:1)-containing hydrogels with no TGF-$\beta$, soluble TGF-$\beta$ or acryloyl-PEG-TGF-$\beta$ at $4 \times 10^{-5}$ nmol/ml in the hydrogel. The control is with no TGF-$\beta$ in the hydrogel.

The results for cells grown in the presence of 0.04 pmol/ml of TGF-β are presented in FIG. 3. More hydroxyproline, and thus more collagen, was produced by SMCs grown in the presence of either soluble or tethered TGF-β than when no TGF-β was present. Additionally, significantly more hydroxyproline was produced when TGF-β was tethered onto the hydrogels than when soluble TGF-β was used.

Additionally, the mechanical properties of hydrogels made with and without TGF-β were examined. Young's modulus, a measure of the stiffness of the scaffold, was significantly higher when TGF-β was tethered to the scaffolds than when no TGF-β was used (66.6±3.7 kPa with tethered TGF-β versus 58.5±1.8 kPa with no TGF-β, p=0.03).

EXAMPLE 2

Dose Response of Aortic Smooth Muscle Cells to TGF-β

Aortic smooth muscle cells were grown on aminophase glass that had 0.5 nmol/cm$^2$ RGDS (SEQ ID NO:1) covalently coupled to the glass. TGF-β was added to the media at 0, 1, or 5 ng/ml (0, $4\times10^{-5}$, $2\times10^{-4}$ nmol/ml). ECM protein production by the cells over a 2-day time period was determined by examining the amount of $^3$H-glycine incorporated into the ECM elaborated by the cells.

Figure 4:
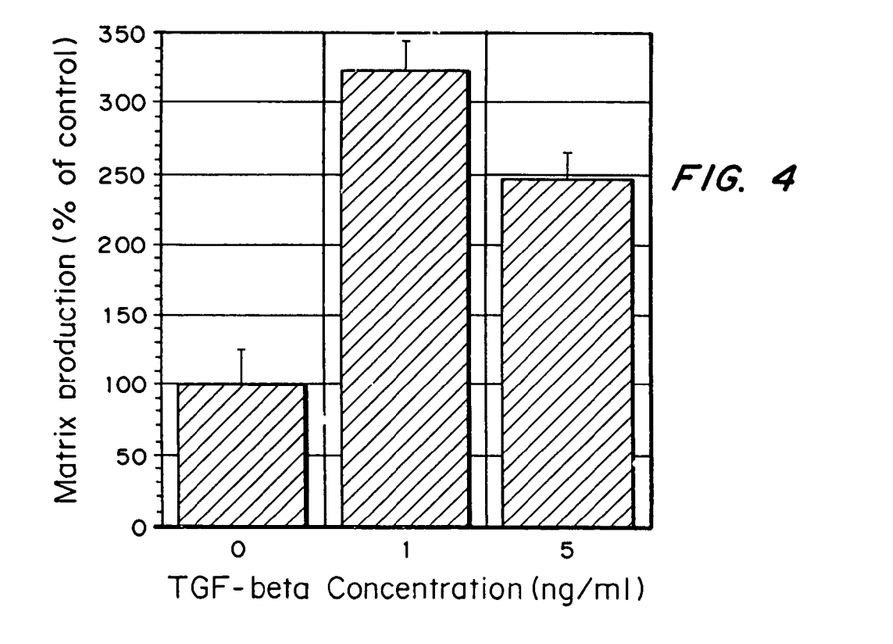
FIG. 4 is a graph of matrix production by SMCs growing on RGDS (SEQ ID NO:1)-modified glass surfaces, as percent of control, as a function of TGF-β concentration (0, 1 and 5 ng/ml).

As seen in FIG. 4, ECM protein production per cell (% of control) was increased when TGF-β was added to the media at both 1 and 5 ng/ml. Further, cell numbers did not increase over the 2 days, despite changes in matrix production per cell, indicating that the presence of TGF-β did not increase proliferation of the SMCs, as seen in the hydrogels.

EXAMPLE 3

Dose Response of Auricular Chondrocytes to TGF-β

Auricular chondrocytes were grown on tissue culture polystyrene with varying amounts of TGF-β added to the media: 0, 1, 5, 10, 25, or 100 ng/ml. ECM protein production by the cells over a 2-day time period was determined by examining the amount of $^3$H-glycine incorporated into the ECM elaborated by the cells.

Figure 5:
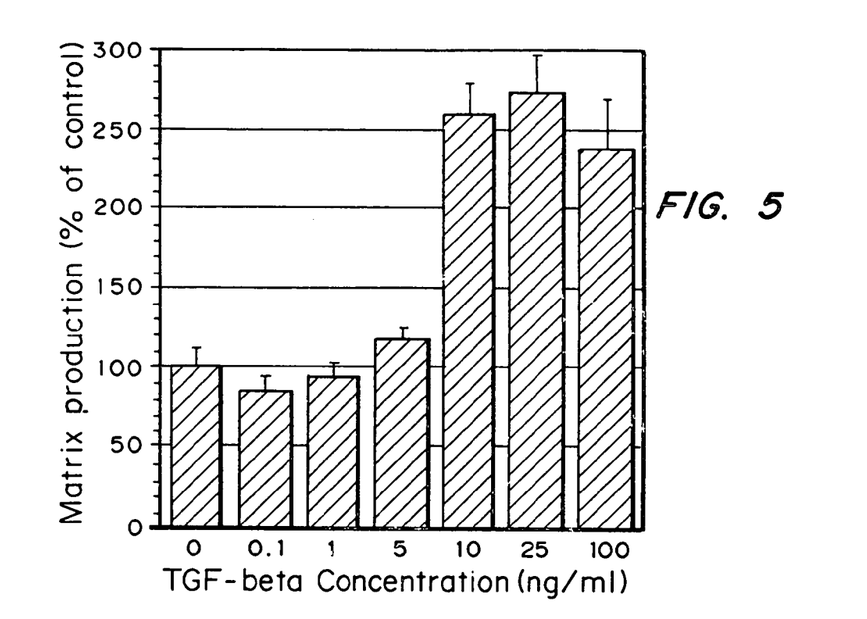
FIG. 5 is a graph of matrix production, as percent of control, by auricular chondrocytes growing on tissue culture polystyrene in the presence of varying amounts of TGF-β (0, 0.1, 1, 5, 10, 25 and 100 ng/ml) in the media. The control is with no TGF-β in the media.
Figure 6:
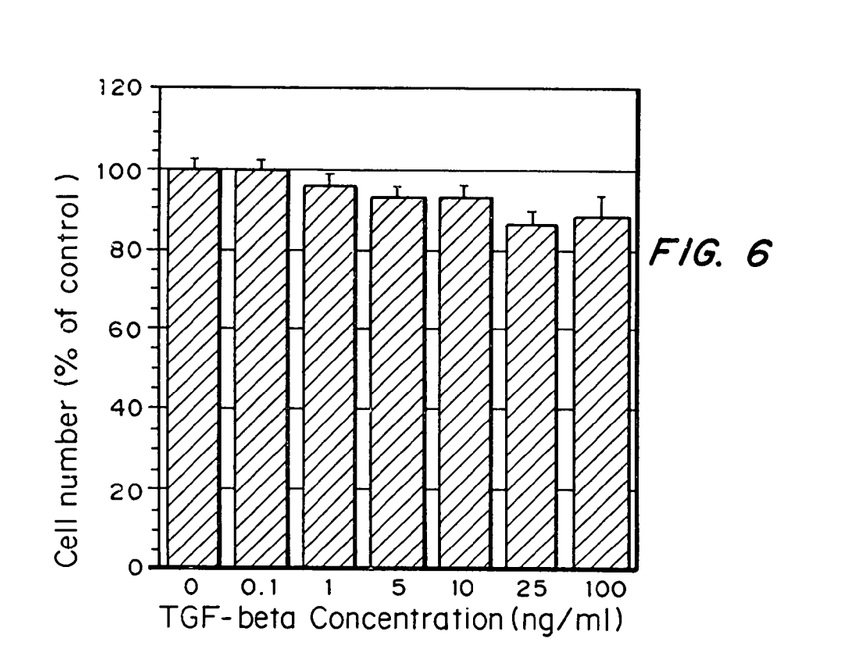
FIG. 6 is a graph of cell number, as percent of control, by auricular chondrocytes growing on tissue culture polystyrene in the presence of varying amounts of TGF-β (0, 0.1, 1, 5, 10, 25 and 100 ng/ml) in the media. The control is with no TGF-β in the media.

As seen in FIG. 5, ECM protein production per cell was increased when TGF-β was added to the media at concentrations above 1 ng/ml, with an optimal concentration of 25 ng/ml (1×10$^{-3}$ nmol/ml). Further, cell numbers did not increase over the 2 days (see FIG. 6), despite changes in matrix production per cell, indicating that the presence of TGF-β did not increase proliferation of the chondrocytes.

EXAMPLE 4

Increase in Matrix Production in the Presence of Ascorbic Acid

Aortic smooth muscle cells and auricular chondrocytes were grown on tissue culture polystyrene with and without 50 μg/ml ascorbic acid added to the media. ECM protein production by the cells over a 2-day time period was determined by examining the amount of $^3$H-glycine incorporated into the ECM elaborated by the cells.

Figure 7:
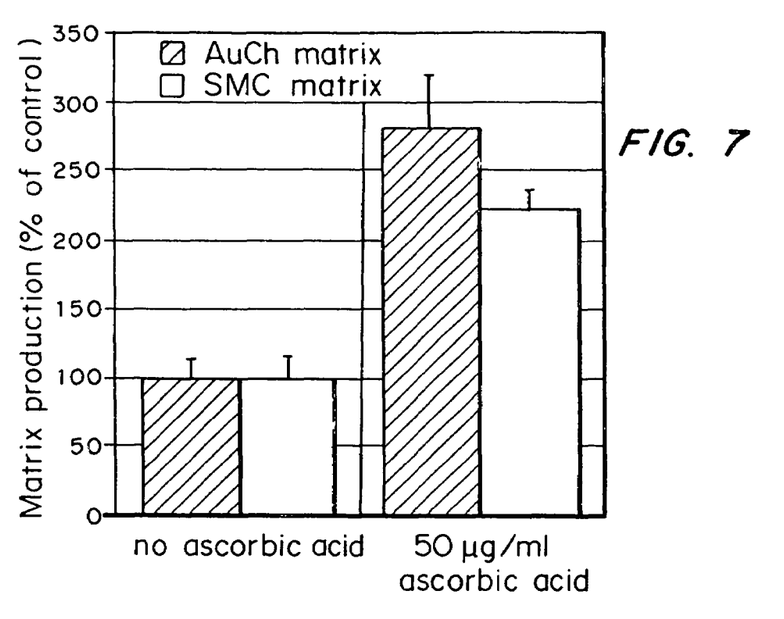
FIG. 7 is a graph of matrix production, as percent of control, by auricular chondrocytes and aortic smooth muscle cells growing on tissue culture polystyrene in the presence of 0 and 50 μg/ml ascorbic acid in the media. The control is with no ascorbic acid in the media.
Figure 8:
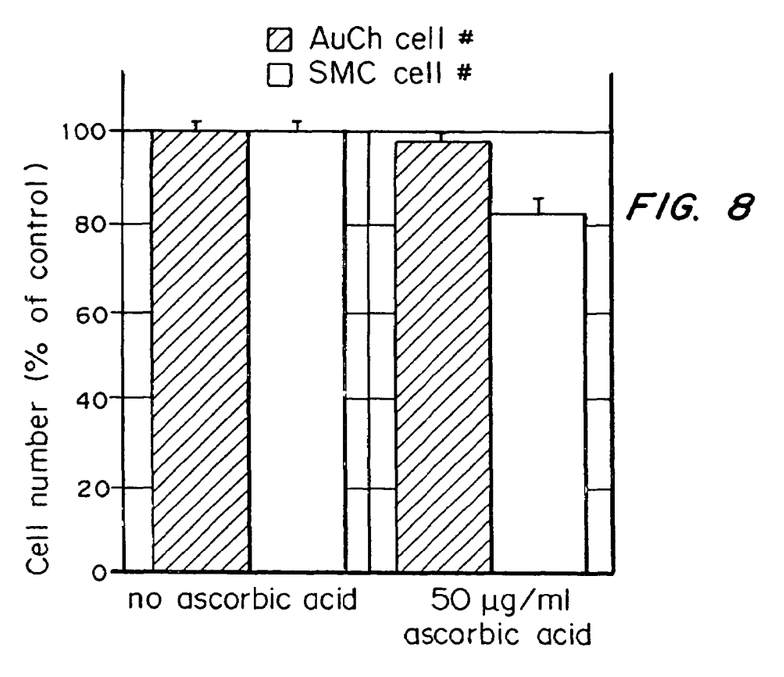
FIG. 8 is a graph of cell number, as percent of control, by auricular chondrocytes and aortic smooth muscle cells growing on tissue culture polystyrene in the presence of 0 and 50 μg/ml ascorbic acid in the media. The control is with no ascorbic acid in the media.

As seen in FIG. 7, ECM protein production per cell was increased in the presence of ascorbic acid for both SMCs (light gray) and chondrocytes (dark gray). Further, cell numbers did not increase over the 2 days (FIG. 8), despite changes in matrix production per cell, indicating that the presence of ascorbic acid did not increase proliferation of the smooth muscle cells (light Grey) or the chondrocytes (dark Grey).

Modifications and variations of these scaffolds and method for preparation and use thereof will be obvious to those skilled in the art and are intended to be encompassed by the following claims.

We claim:

1. A method for making a tissue engineering scaffold for inducing formation of extracellular matrix by cells bound to the scaffold comprising covalently coupling matrix-enhancing molecules are selected from the group consisting of TGF-β, angiotensin II, insulin-like growth factor and ascorbic acid to the scaffold in an effective density to elicit production of extracellular matrix without increasing cellular proliferation, wherein when the matrix-enhancing molecules are TGF-β, the TGF-β is covalently coupled to the matrix by a polymer tether having a molecular weight between 2000 and 6000 and is in a density between 1 and 100 ng TGF-β/ml or in a concentration of between about $4 \times 10^{-6}$ and $4 \times 10^{-3}$ nmol/ml.

2. The method of claim 1 further comprising attaching cells to the scaffold.

3. The method of claim 1 wherein the matrix-enhancing molecules are angiotensin II.

4. The method of claim 1 wherein the matrix-enhancing molecules are insulin-like growth factor.

5. The method of claim 1 wherein the matrix-enhancing molecules are ascorbic acid.

6. The method of claim 1 wherein the scaffold is a hydrogel.

7. The method of claim 6 wherein the hydrogel is formed of a polymer selected from the group consisting of alginate, collagen, hyaluronic acid, and polyethylene glycol polymers.

8. The method of claim 6 wherein the matrix-enhancing molecules are TGF-β coupled to the hydrogel in a concentration of between about $4 \times 10^{-6}$ and $4 \times 10^{-3}$ nmol/ml.

9. A method for making a tissue engineering scaffold, the method comprising:
providing a scaffold, a polymer tether, and a matrix-enhancing molecule;
covalently coupling the polymer tether to the scaffold; and
covalently coupling the matrix-enhancing molecule to the scaffold, wherein the matrix-enhancing molecule is present at a concentration sufficient to elicit production of extracellular matrix by a cell attached to the tissue engineering scaffold without increasing cellular proliferation of the attached cell.

10. The method of claim 9 further comprising providing a cell attached to the tissue engineering scaffold.

11. The method of claim 9 further comprising providing a cell attached to the tissue engineering scaffold, wherein the cell is attached to the tissue engineering scaffold by constraining the cell within the scaffold.

12. The method of claim 9 further comprising providing a cell attached to the tissue engineering scaffold, wherein the cell is selected from the group consisting of smooth muscle cells, endothelial cells, fibroblasts, chondrocytes, and combinations thereof.

13. The method of claim 9 wherein the matrix enhancing molecule is TGF-β.

14. The method of claim 9 wherein the matrix enhancing molecule is TGF-β and the TGF-β is present at a density of between 1 and 100 ng TGF-β/ml or in a concentration of between about $4 \times 10^{-6}$ and $4 \times 10^{-3}$ nmol/ml.

15. The method of claim 9 wherein the matrix-enhancing molecule is angiotensin II.

16. The method of claim 9 wherein the matrix-enhancing molecule is insulin-like growth factor.

17. The method of claim 9 wherein the matrix-enhancing molecule is ascorbic acid.

18. The method of claim 9 wherein the scaffold is a hydrogel.

19. The method of claim 9 wherein the scaffold is a hydrogel comprising a polymer selected from the group consisting of alginate, collagen, hyaluronic acid, polyethylene glycol polymers, and combinations thereof.

20. The method of claim 9 wherein the polymer tether has a molecular weight between 200 and 10,000.

* * * * *